United States Patent
Zornow

(10) Patent No.: US 8,517,981 B2
(45) Date of Patent: Aug. 27, 2013

(54) METHOD AND APPARATUS FOR PREVENTION OF APNEA

(75) Inventor: Mark H. Zornow, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 52 days.

(21) Appl. No.: 13/148,758

(22) PCT Filed: Feb. 10, 2010

(86) PCT No.: PCT/US2010/023730
§ 371 (c)(1),
(2), (4) Date: Aug. 10, 2011

(87) PCT Pub. No.: WO2010/093677
PCT Pub. Date: Aug. 19, 2010

(65) Prior Publication Data
US 2011/0313262 A1    Dec. 22, 2011

Related U.S. Application Data

(60) Provisional application No. 61/152,153, filed on Feb. 12, 2009.

(51) Int. Cl.
*A61M 31/00*    (2006.01)
*A61M 15/00*    (2006.01)
*A61B 5/00*    (2006.01)
*A61N 1/00*    (2006.01)

(52) U.S. Cl.
USPC ........ 604/66; 128/200.24; 600/300; 600/323; 307/42

(58) Field of Classification Search
USPC .............. 604/66; 128/200.24; 600/300, 323, 600/529; 702/19; 607/42, 62; 340/573.1
See application file for complete search history.

(56) References Cited

U.S. PATENT DOCUMENTS

| | | | |
|---|---|---|---|
| 4,195,626 A * | 4/1980 | Schweizer | 600/587 |
| 5,329,931 A | 7/1994 | Clauson et al. | |
| 5,423,327 A * | 6/1995 | Clauson et al. | 600/322 |
| 5,605,151 A * | 2/1997 | Lynn | 600/323 |
| 5,765,563 A * | 6/1998 | Vander Schaaf | 600/538 |
| 5,865,736 A * | 2/1999 | Baker et al. | 600/323 |
| 6,754,516 B2 * | 6/2004 | Mannheimer | 600/323 |
| 7,387,608 B2 * | 6/2008 | Dunlop et al. | 600/500 |
| 8,146,591 B2 * | 4/2012 | Niklewski et al. | 128/204.23 |
| 2005/0222502 A1 * | 10/2005 | Cooper | 600/323 |
| 2006/0128605 A1 * | 6/2006 | Shibahara et al. | 514/2 |
| 2007/0191697 A1 * | 8/2007 | Lynn et al. | 600/323 |
| 2008/0058612 A1 | 3/2008 | Ohyu et al. | |
| 2008/0216835 A1 * | 9/2008 | McGinnis et al. | 128/204.23 |
| 2008/0243393 A1 * | 10/2008 | Yamamoto et al. | 702/19 |

FOREIGN PATENT DOCUMENTS

| EP | 0504725 A2 | 9/1992 |
|---|---|---|
| EP | 1964514 A1 | 9/2008 |

* cited by examiner

*Primary Examiner* — Quynh-Nhu H Vu
(74) *Attorney, Agent, or Firm* — Schwabe, Williamson & Wyatt

(57) ABSTRACT

Embodiments provide a continuous monitor of a patient's oxygenation and/or respiration coupled to a device configured to stimulate the patient's respiratory drive and/or summon medical assistance. In embodiments, there are provided systems, devices, and methods to assist in preventing patients from overdosing themselves with narcotics post-surgery. In embodiments, an apnea prevention device (APD) may utilize a commercially available pulse oximeter and/or a respiratory monitor to continuously monitor a patient's level of oxygenation/respiration. Should a patient develop respiratory depression or apnea and begin to desaturate, an APD may, using a proprietary method, trigger a sequence of staged responses to reverse worsening hypoxia.

9 Claims, 7 Drawing Sheets

METHOD AND APPARATUS FOR PREVENTION OF APNEA

CROSS REFERENCE TO RELATED APPLICATIONS

The present application is related to U.S. Provisional Patent Application No. 61/152,153, filed Feb. 12, 2009, entitled "Method and Apparatus for Prevention of Apnea," the entire disclosure of which is hereby incorporated by reference in its entirety.

TECHNICAL FIELD

Embodiments herein relate to the field of medical devices, and, more specifically, to a method and apparatus for prevention of apnea.

BACKGROUND

In recent years, there have been increasingly aggressive attempts to treat postoperative pain. This trend was instigated, in part, when the Joint Commission on Accreditations of Hospital Organizations (JCAHO) designated pain as the "fifth" vital sign. Unfortunately, as an unintended consequence, more and more patients are being overdosed with narcotics, either from Patient Controlled Analgesia (PCA) devices or via neuraxial narcotics (epidurals). This has resulted in more and more cases of profound respiratory depression, apnea, hypoxemia and brain injury or death. The literature would suggest that between 0.1% and 1% of patients on PCA will have one or more episodes of serious respiratory depression. The Anesthesia Patient Safety Foundation (APSF), which has been recognized as a leader in the field of patient safety by the Institute of Medicine, has identified narcotic-induced postoperative respiratory depression as a major cause of perioperative morbidity. Current monitoring modalities are inadequate to detect and treat the respiratory depression seen in post operative patients. Intermittent nursing assessments, even if done on a frequent basis, are not adequate to detect the rapid onset of airway obstruction, apnea, and hypoxia that can occur in many of these patients. Continuous nursing observation, as in an ICU setting, is cost-prohibitive and simply not practical given the large number of patients at risk.

Currently, there is no good way to detect and treat episodes of postoperative respiratory depression. Even frequent nursing checks (every two hours) are insufficient to detect and treat apnea and hypoxemia in a timely fashion. Patients who are using PCAs that have been set for a 10 minute lockout could administer as many as 12 IV boluses of narcotics to themselves between nursing checks. Continuous monitoring of these patients in ICU settings with 1:1 or 1:2 staffing is simply impractical given the large number of patients who would need monitoring.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
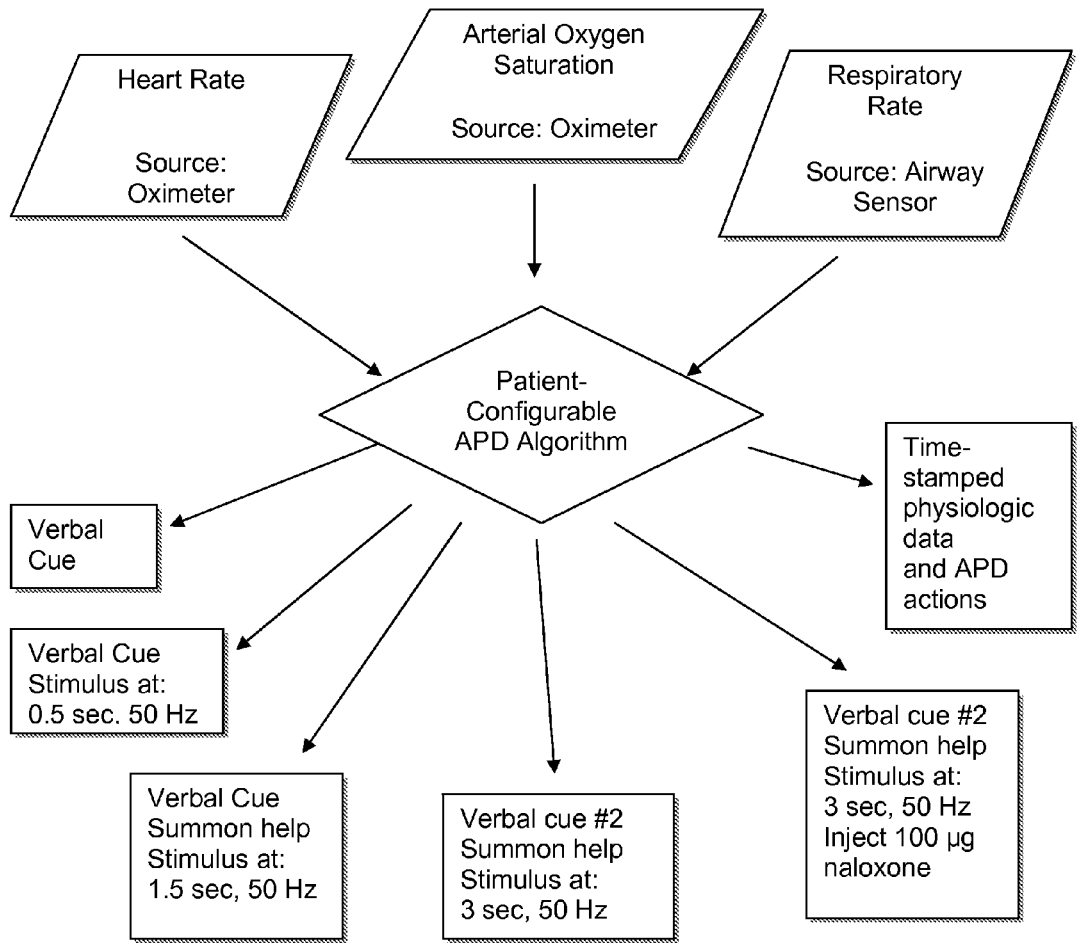
FIG. 1 is a flowchart showing the functions of a sleep apnea prevention device, including collection of physiologic data, triggering of interventions (auditory, tactile) and logging of data in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems for prevention of apnea are provided. In exemplary embodiments, a computing device may be endowed with one or more components of the disclosed apparatuses and/or systems and may be employed to perform one or more methods as disclosed herein.

Embodiments herein provide a continuous monitor of a patient's oxygenation and/or respiration coupled to a device configured to stimulate the patient's respiratory drive and/or summon medical assistance. In accordance with an embodiment, an apnea prevention device (APD) may be configured to decrease the incidence of postoperative respiratory depression, apnea, and/or hypoxic brain injury by monitoring respiratory function and delivering incremental stimuli (verbal, tactile, etc.) when there is evidence of respiratory depression.

An APD may be used on postoperative surgical wards in patients receiving neuraxial or intravenous narcotics for surgical pain. In addition, an APD would be useful during procedures involving moderate to deep sedation. Examples of such procedures include endoscopies, interventional radiology procedures, imaging studies (MRI, angiography), minor surgery, etc. Without an APD, one of the providers for each of these procedures is often preoccupied with providing verbal and/or tactile stimulation to the patient to keep the patient's respiratory rate and oxygen saturation at an acceptable level. While performing this important task, that provider is unavailable to assist with the timely completion of the procedure. This task of monitoring and maintaining adequate ventilation could be delegated to the APD which would allow for fewer interruptions of the procedure, its more timely completion, and possibly reducing the number of providers required for the procedure, thereby resulting in significant cost savings.

In embodiments, there are provided systems, devices, and methods to assist in preventing patients from overdosing themselves with narcotics post-surgery. In some situations, patients are permitted to post-operatively regulate their pain meds. Sometimes this leads to the unfortunate effect of causing serious respiratory depression (the patients can put themselves into a coma or worse), which is a major cause of peri-operative morbidity. Systems in accordance with embodiments herein detect respiratory depression and may noninvasively and then invasively (if necessary) treat the respiratory depression to prevent coma/death, prior to medical provider intervention/help.

In embodiments, an APD may utilize a pulse oximeter to continuously monitor a patient's level of oxygenation. Pulse oximeters are commonly used in acute care areas of hospitals and non-invasively monitor arterial oxygen saturation by measuring changes in the transmission of light through perfused tissue (e.g., a fingertip). Should a patient develop respiratory depression or apnea and begin to desaturate at or below an acceptable level, an APD may, using a triggering method, trigger a sequence of staged responses to worsening hypoxia.

Embodiments may also utilize a commercially available respiratory monitor to continuously monitor a patient's level of respiration. A respiratory monitor may be used instead of, or in addition to, a pulse oximeter.

In embodiments, a patient-specific algorithm analyzes one or both of the respiratory rate and oxygenation data to determine when and what type of interventions should be delivered. Multiple critical thresholds for both oxygen saturation and respiratory rate may be entered into the APD which will then use these criteria to minimize the delivery of unnecessary interventions, while assuring the delivery of appropriate interventions should respiratory depression occur. For example, a threshold or predefined range of oxygen saturation below 90%, below 85%, etc. may be established. An exemplary respiratory rate of less than 3, 4, or 5 breaths per minute could be established to trigger an intervention by the APD. In embodiments, a single threshold may be used, or as the condition worsens (lower oxygen saturation or even fewer breaths per minute), the interventions may change, such as by increasing the severity of the stimulus.

In an embodiment, for mild hypoxia (saturations in the range of 85-90%), the APD may play a prerecorded, patient-specific verbal stimulus to breathe ("MR. JONES, TAKE A DEEP BREATH!"). Should hypoxia progress below 85%, the APD may notify/summon medical assistance through any of a variety of communication links and trigger a constant current stimulator to deliver increasingly strong impulses via surface electrodes (EKG pads) to a peripheral nerve. These impulses may be configured to range in intensity from mildly uncomfortable to painful in nature. The purpose of the stimulation is primarily to arouse the patient to the point that normal respiration resumes. Should hypoxia progress despite the verbal encouragement to breathe and the arousal stimulus provided by the nerve stimulator, the APD may administer a bolus dose of Naloxone, a specific and fast acting narcotic antagonist, or similar drug through the patient's IV.

In many respects, the APD may duplicate the actions of an intensive care nurse who observes respiratory depression in a patient. Typically, a nurse's first action would be to try to arouse the patient with verbal stimuli. Should that fail, the nurse will often shake the patient or administer a sternal rub while calling for help. Finally, should these attempts to arouse the patient fail, a bolus of Naloxone is generally administered.

In an embodiment, a patient may have a hand-held 'fail safe' button that if activated by the patient, would interrupt the sequence of actions taken by the APD. This safety device would prevent stimuli from being delivered to patients in cases of false positive detection of hypoxia by the pulse oximeter or APD failure, etc.

FIG. 1 is a flowchart showing functions of an apnea prevention device, including collection of physiologic data, triggering of interventions (audible, tactile) and logging of data, such as recording a time-stamped, electronic log of physiologic data of an individual and any delivered stimulus or intervention.

Figure 2:
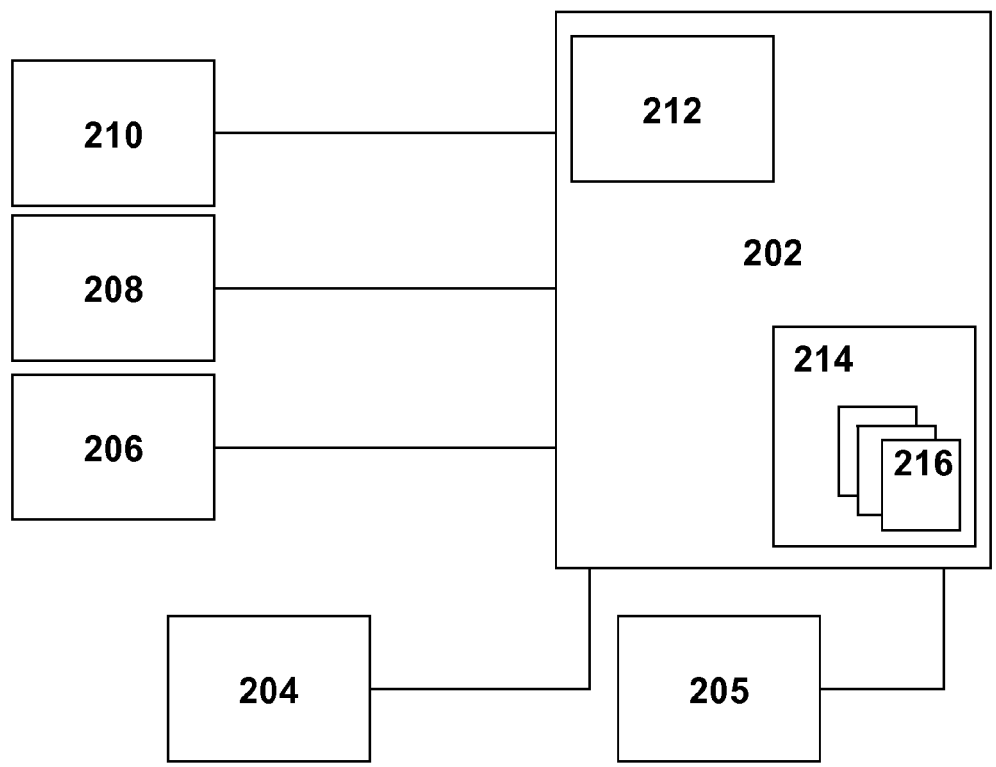
FIG. 2 is a block diagram of a sleep apnea prevention device in accordance with various embodiments.

FIG. 2 is a block diagram of an apnea prevention device showing various components in accordance with embodiments. FIG. 2 shows a computing device 202, such as a laptop computer, desktop computer, etc. Software running on the computing device may be used to acquire physiologic data (heart rate and oxygen saturation) from pulse oximeter 204. Physiologic data may also be acquired from respiratory monitor 205. The system may be programmed to make decisions on what type of interventions to initiate if there is evidence of respiratory depression. Available interventions may include verbal prompts from speaker 206, which may be a loudspeaker, headphones, etc., and cutaneous stimulation from nerve stimulator 208, as well as other means of stimulation. Additional interventions may be provided by a drug delivery device 210 and/or a transmitter 212.

Drug delivery device 210, such as an infusion pump, may be configured to deliver a dose of a narcotic antagonist, such as Naloxone, in response to a particular patient status (e.g., a particular oxygen saturation range or level of respiratory depression). Transmitter 212 may be configured to notify or summon a medical professional (nurse, doctor, etc.) in response to a particular patient status. Transmitter 212 may be part of computing device 202 or may be a separate component coupled to computing device 202 by wire or wirelessly.

Computing device 202 may be coupled to a computer-readable medium 214 (hard disk, floppy disk, compact disk, etc.) having instructions 216 stored thereon. Instructions 216 are configured to cause computing device 202 to perform certain actions as a result of execution of instructions 216.

The program/instructions include error checking routines to decrease the incidence of false alarms and to address possible loss-of-signal events. The program/instructions allow the user to customize the critical oxygen saturation and/or resppiration parameters at which the various interventions are triggered and logs all data to a patient-specific file.

Pulse oximeter 204, respiratory monitor 205, speaker 206, nerve stimulator 208, and drug delivery device 210 may each independently be coupled to computing device 202 wirelessly or by wire, such as by a medical grade cable, USB cable, or other connector.

Speaker(s) 206 may be placed in close proximity to a patient's ears. Voice prompts or other audible or visible indicators to encourage the patient to breathe may be delivered, when indicated, from computing device 202, such as from a file stored in computing device 202. Speaker(s) 206 may be connected to computing device 202 by the audio-out port.

A commercially available nerve stimulator 208, such as a peripheral nerve stimulator, may be used to deliver cutaneous stimulation when a method/apparatus detects evidence of respiratory depression. A stimulus may be delivered to the skin of the patient by way of surface electrode pads (EKG pads). In an embodiment, stimulator 208 may be configured to deliver stimulus to the skin over the dorsum of the hand, in particular positioned at the thenar eminence. Stimulus intensity (mA), pulse duration, such as 0.5-1.5 seconds, frequency, and/or regularity of stimulus may be adjusted to provide stimuli ranging from mild to intense depending on the severity of the respiratory depression.

Pulse oximeter 204 may be a commercially available pulse oximeter. The sensor for pulse oximeter 204 may be a light emitting diode/detector which is non-invasively applied to a finger tip. Heart rate and arterial oxygen saturation may be obtained from this sensor and then transmitted to computing device 202.

In an embodiment, an apnea prevention device may utilize various methods. The following provides a description of a method that may be used to trigger interventions in response to falling oxygen saturations.

For this exemplary method, the following definitions may be used:
Pulseox are the last X readings from the pulse oximeter. For an intervention to be triggered, all X number of data points need to meet certain criteria;
Sat1, Sat2, Sat3, Sat4 are user (medical professional) entered limits for saturation;
Intervention1, Intervention2, Intervention3 and Intervention4 are actions the program should initiate when certain Sat criteria are met;
Intervention1 is to play the WAV1 file: "Take a deep breath right now. Breathe!";
Intervention2 is to play the WAV2 file "Come on. Take a deep breath RIGHT NOW!" and to deliver a 0.5 second tetanic stimulus via surface electrodes;
Intervention3 is to play the WAV2 file again and to deliver a 1.5 second tetanic stimulus via surface electrodes;
Intervention4 is to play WAV2 file again and to deliver a 3.0 second tetanic stimulus via surface electrodes.

The default mode is to do no intervention. There will be a delay, such as a pause of 20 seconds, after each intervention to allow the patient time to respond before the program can trigger another intervention.

In an embodiment, a particular method may provide that:
if Pulseox is between Sat1 and Sat2, do Intervention1;
if Pulseox is between Sat2 and Sat3, do Intervention2;
if Pulseox is between Sat3 and Sat 4, do Intervention3; and
if Pulseox is less than Sat4, do Intervention4.

If desired, one or both of the endpoints may be included to trigger an intervention. For example, if Pulseox is the same as Sat1, that may trigger Intervention1. The method may be established such that if Pulseox is the same as Sat2, the determined level may trigger Intervention1 or it may trigger Intervention2.

An alternative method may utilize the following parameters:
if saturation is sustained above 90% for 10 seconds, do nothing;
if saturation is below 90% for more than 10 seconds, trigger a voice prompt;
if saturation is below 85% for more than 10 seconds, deliver a 0.5 second 50 Hz stimulus at 20 mA, continue voice prompt, contact medical staff;
if saturation is below 80% for more than 10 seconds, increase mA to 40 and deliver repetitive 0.5 second 50Hz stimuli, change to a different voice prompt (for this example, referred to as prompt number 2); and
if saturation is below 75% for more than 10 seconds, deliver 4 second stimulus at 50 mA, repeat every 10 seconds, continue voice prompt number 2, administer 400 μg bolus does of Naloxone.

In embodiments, suitable tactile stimulus ranges may be 0.5-5.0 seconds in duration, 40-60 Hz, and 10-60 mA. These parameters may be controlled/adjusted. Other values and ranges may be used as needed/desired.

In embodiments, an apnea prevention device may include a test/display mode to allow for testing/demonstration of the program without actual pulse oximetry data. The user can enter saturation values while the program is running to demonstrate proper function and delivery of the interventions.

In an embodiment, an apnea prevention device may be programmed for the desired levels of saturation or respiration at which interventions are triggered. In embodiments, voice prompts may be modified and customized. In embodiments, stimulus durations may be adjusted. The system may permit adjustment of the number of pulse oximeter readings to be analyzed prior to triggering an intervention. In an embodiment, a data log of physiologic values and triggering of interventions may also be provided.

In an embodiment, an interface with a paging system or a Wi-Fi enabled device (e.g. Vocera) or other such devices may be provided to notify health care providers of loss of signal or critical levels of oxygen saturation. Once notified of the potential for patient harm, providers may intervene by decreasing dosing or transferring the patient to a higher acuity setting for closer supervision. When the depth or frequency of the respiratory depression reaches a preset threshold, medical assistance may be summoned by the integrated communication pathway. Once the provider has reviewed the frequency and depth of the episodes, a decision may be made as to the appropriate treatment.

Other methods may be provided that include rate of fall of oxygen saturation, respiratory data (number of breaths per minute), and/or heart rate with oxygen saturation levels.

In an embodiment, an interface with a respiratory monitor (capnometer, acoustic respiratory sensor, piezo-electric microphone, etc.) may be provided to add an additional parameter of ventilation to oximetry. Addition of this capability may require modification of the methods/programs triggering interventions to reduce the incidence of false alarms and improve the apnea prevention device's ability to treat respiratory depression.

The stimulating electrodes may be incorporated either into the oximetry sensor, or, if an acoustic respiratory sensor is used, into that device. Headphones are likely to be impractical for use on a ward setting, hence placing the speakers used to deliver the verbal stimulus into the pillow or side-rails of the bed may be more suitable options. Both of these modifications reduce the number of wires connected to the patient and thereby decrease the likelihood of device failure.

In an exemplary embodiment, a prototype APD was used including a laptop computer running custom software, a pulse oximeter, and a nerve stimulator. Specifically, the computer was running a program written in C# (Oxymon v. 1.03). A Masimo SET oximeter was connected to this computer by way of a RS-232 port. Averaging time for saturations on the oximeter was set to the minimum of 2 seconds. A DigiStimII (NeuroTechnologies, Kerrville, Tex.) peripheral nerve stimulator with variable current output was also connected to the laptop by means of a USB port. Oxygen saturation data were acquired by the program from the pulse oximeter and stimuli to the patient were delivered either by headphones (verbal prompts) or a nerve stimulator (cutaneous). The APD program was written to analyze oximetry data and when indicated, deliver a series of stimuli of increasing intensity to arouse patients from narcosis.

The device was tested on surgical patients in the post-anesthesia care unit (PACU). Each intervention delivered by the APD was scored by an observer as either a success (the patient took a large tidal volume breath and oxygen saturations increased) or a failure (no response to intervention). The APD maintained a data log of oxygen saturations and interventions. In a subset of patients, it was possible to compare the functioning of the APD with routine nursing care.

Ten patients were studied for this example. A total of 125 interventions were delivered by the APD to these patients with a 97% success rate. The depth and duration of desaturations were less when the APD was in use than when patients received routine 1:1 nursing care.

In this particular embodiment, the APD was programmable with: 1) up to four threshold values for oxygen saturation, 2) the number of consecutive saturations that must fall below a critical (threshold) level before the APD triggers an intervention (minimizes false triggering), and 3) the lock-out period between interventions (time period that allows patients to respond to an intervention and allows the saturations to increase). Whenever any of the four user-entered threshold saturations were exceeded, the laptop computer triggered either a patient-specific verbal stimulus (e.g., "BOB! Take a deep breath! BREATHE!") or a graded (for example 0.5-1.5 second) electrical stimulus to the skin followed by the voice prompt. Voice prompts were delivered via foam headphones positioned over the patient's ears. The volume was adjustable, but was initially set at 86 decibels (approximately 6 dB above ambient). For this example, the saturation threshold values were set relatively high to ensure sufficient triggering of the device to verify proper function.

The parameters used in this example were as follows: Threshold saturations: 97%, 95%, 93%, and 91%; Data verification: 3 consecutive saturations below critical value; Lock-out interval: 60 seconds. The interventions that were delivered are as follows:

Intervention #1: For 3 or more consecutive saturations below 97%, administer patient specific verbal prompt (e.g., "BOB! Take a deep breathe right now. BREATHE!")

Intervention #2: For 3 or more consecutive saturations below 95%, deliver 0.5 second, 50 Hz stimulus to dorsum of hand followed by a more emphatic patient-specific verbal stimulus (using the patient's name or other specific identifier).

Intervention #3: For 3 or more consecutive saturations below 93%, deliver 1.0 second, 50 Hz stimulus to dorsum of hand followed by verbal prompt.

Intervention #4: For 3 or more consecutive saturations below 91%, deliver 1.5 second, 50 Hz stimulus to dorsum of hand followed by verbal prompt.

The demographics of included patients are shown in Table 1. Patients were classified as having pulmonary pathology if they were current cigarette smokers, had a history of reactive airway disease, or had multiple pulmonary emboli. Risk assessment for OSA was part of the preoperative evaluation. ASA=Preop physical status, BMI=body mass index.

TABLE 1

| Pt. | Age | ASA | BMI | Pulmonary Pathology | Risk OSA | Opiod Use |
|---|---|---|---|---|---|---|
| MP | 63 | 2 | 41 | no | yes | yes |
| CB | 80 | 3 | 26 | no | no | yes |
| EC | 58 | 3 | 35 | yes | no | yes |
| JH | 57 | 3 | 48 | yes | yes | yes |
| YE | 73 | 2 | 20 | yes | no | yes |
| NK | 62 | 2 | 31 | no | no | yes |
| EW | 81 | 3 | 34 | yes | yes | yes |
| JT | 53 | 2 | 33 | yes | yes | no |
| MB | 39 | 2 | 24 | yes | no | yes |
| TH | 37 | 3 | 35 | yes | yes | no |

The mean stimulus current used during the study was 8.4 mA. A total of 125 interventions were delivered by the APD to ten patients with an overall success rate of 97% (see Table 2 below). In Table 2, APD1=verbal prompt, and APD2-4=cutaneous stimulation for 0.5, 1.0 or 1.5 seconds followed by a verbal prompt. Although on occasion a given intervention might fail, higher levels of stimulation were successful. In no instance was it necessary for a nurse to intervene to rescue a patient from an apneic episode while the APD was functioning. No patient withdrew from the study or voiced concern or distress associated with either the verbal prompts or the cutaneous stimulation.

TABLE 2

|  | APD1 | APD2 | APD3 | APD4 | TOTAL |
|---|---|---|---|---|---|
| Delivered | 81 | 14 | 15 | 15 | 125 |
| Successful | 77 | 14 | 15 | 15 | 121 |
| Success Rate | 95% | 100% | 100% | 100% | 97% |

Plots of oxygen saturation vs. time are presented in FIGS. 3-7 for that subset of patients for whom functioning of the APD could be compared with routine nursing care. Hypoxic episodes were more profound ($p<0.0008$) and the frequency of nursing interventions were much greater when the APD interventions were disabled.

Figure 3:
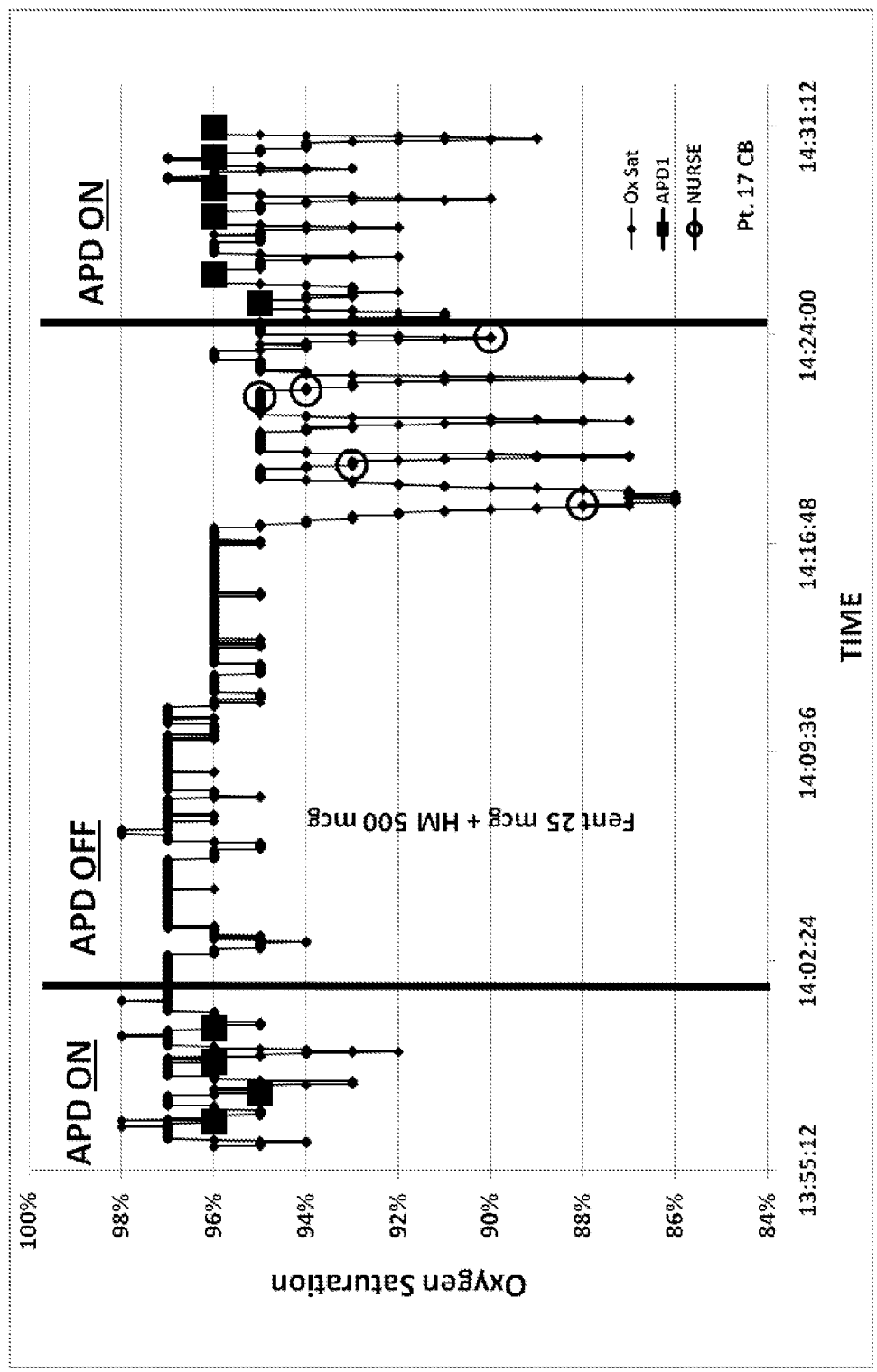
FIGS. 3-7 provide plots of oxygen saturation vs. time for select patients in accordance with embodiments herein.

FIG. 3 shows data for patient CB from Table 1 illustrating oxygen saturations v. time. Note that about 8 minutes after the administration of fentanyl and dilaudid, the patient developed apneic episodes as evidenced by deep desaturations (nadir of 86% at 14:18) which required frequent verbal and tactile prompting by the PACU nurse. When the APD function was resumed at approximately 14:24, no further interventions by the nurse were needed and the patient's saturations remained in the acceptable range without nursing interventions.

Figure 4:
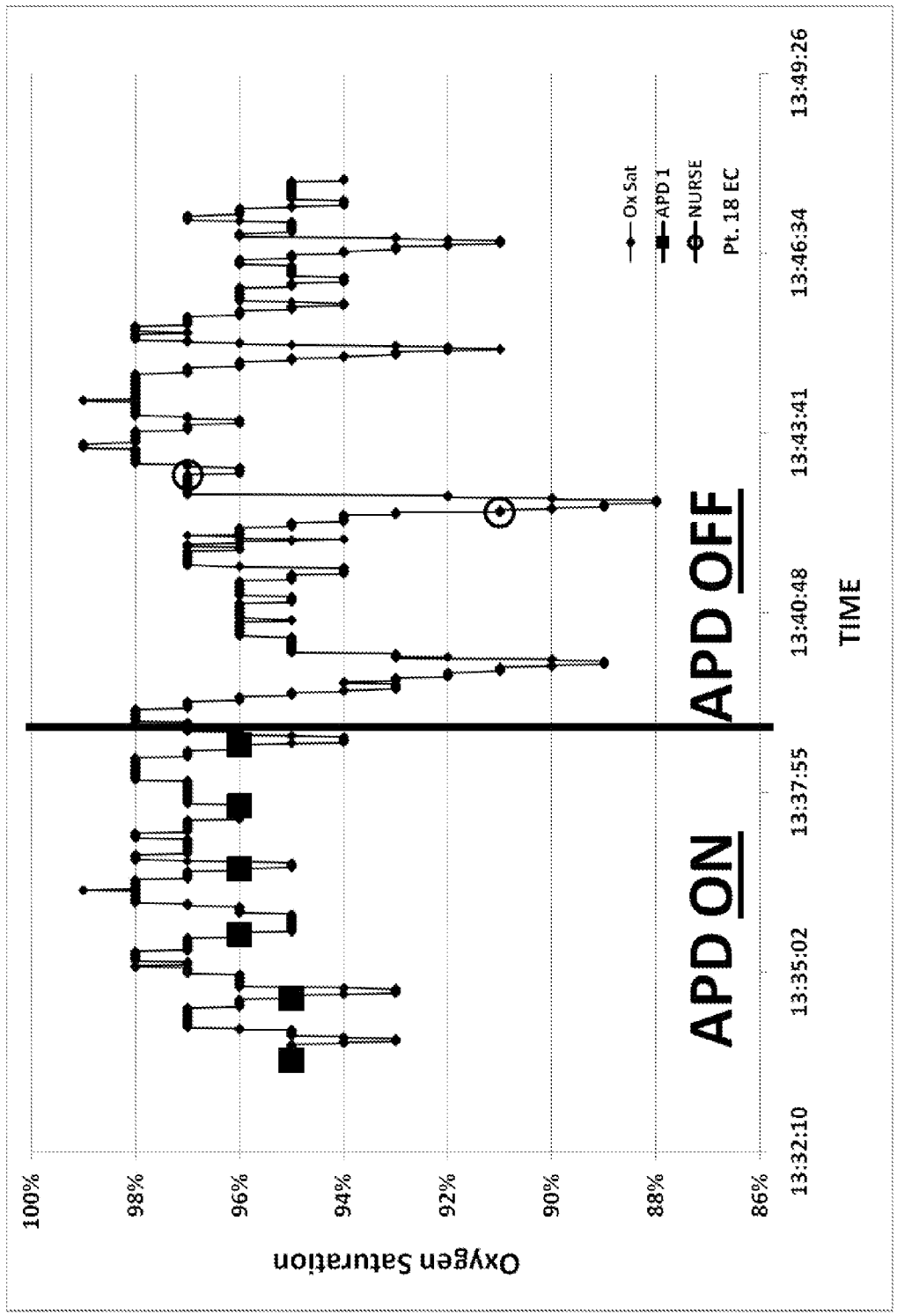

FIG. 4 shows data for patient EC from Table 1 illustrating oxygen saturations v. time. Note that oxygen saturations are better maintained by the APD than by 1:1 PACU nursing supervision. APD1=Verbal prompt by APD. Nurse=verbal prompt by nurse.

Figure 5:
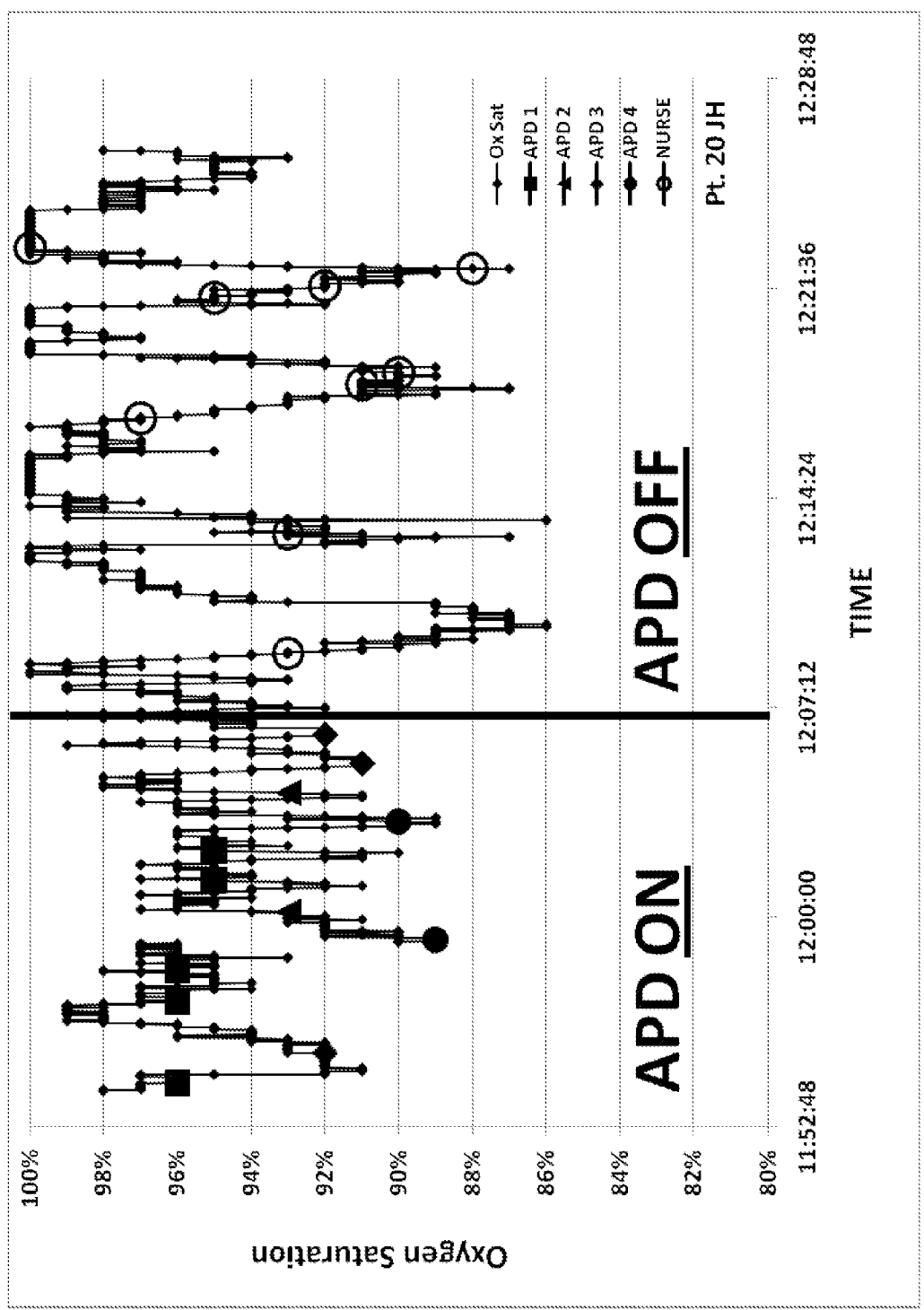

FIG. 5 shows data for patient JH from Table 1 illustrating oxygen saturations v. time. For patient JH, oxygen saturations are better maintained by the APD with no nursing interventions from 11:53 until the device is turned off at 12:06. Subsequently, there are more profound and prolonged desaturations despite frequent nursing interventions. APD1=Verbal prompt by APD. APD2=0.5 second cutaneous stimulus followed by verbal prompt. APD3=1.0 second cutaneous stimulus followed by verbal prompt. APD4=1.5 second cutaneous stimulus followed by verbal prompt. Nurse=verbal prompt by nurse.

Figure 6:
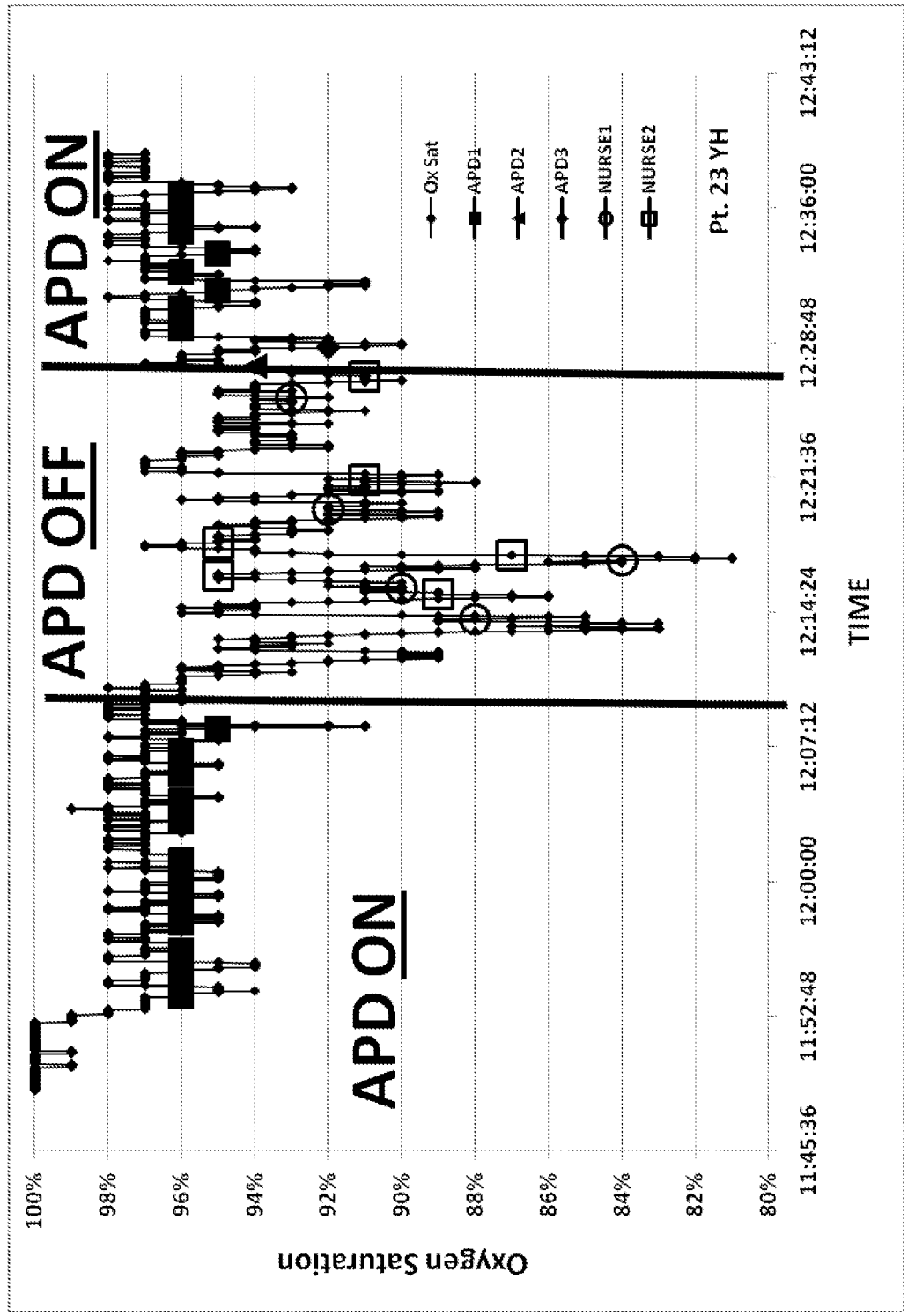

FIG. 6 shows data for patient YH from Table 1 illustrating oxygen saturations v. time. Note profound desaturations (nadir of 81% at 12:17), despite frequent nursing interventions when the APD was disabled. APD1=Verbal prompt by APD. APD2=0.5 second cutaneous stimulus followed by verbal prompt. APD3=1.0 second cutaneous stimulus followed by verbal prompt. Nurse1=verbal prompt by nurse. Nurse2=tactile stimulus by nurse followed by verbal prompt.

Figure 7:
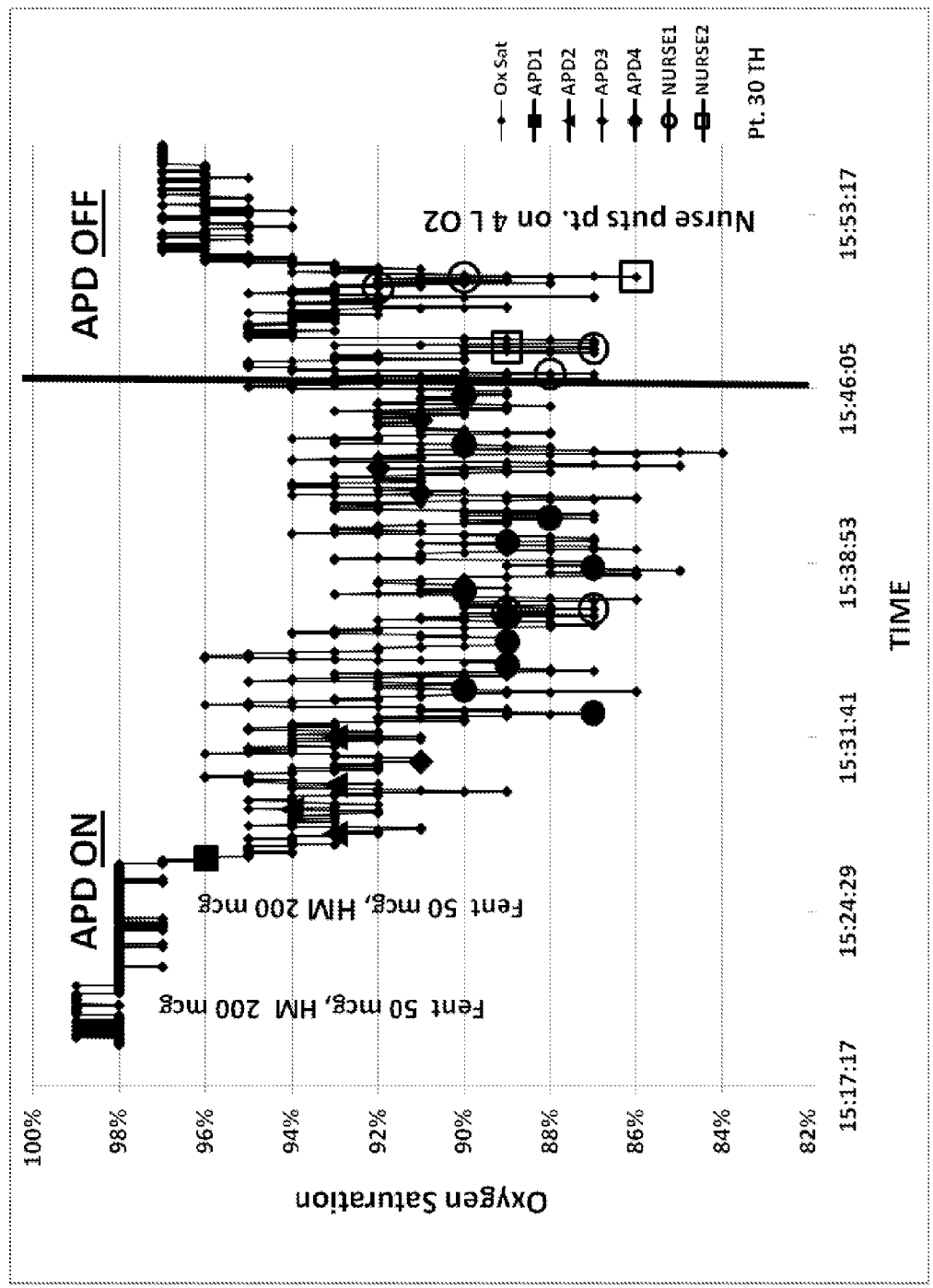

FIG. 7 shows data for patient TH from Table 1 illustrating oxygen saturations v. time. Note that profound and repeated desaturations after the second dose of narcotics requiring repeated interventions by APD. When APD interventions were turned OFF at 15:46, the patient required such frequent interventions (both verbal and tactile) by the PACU nurse that she decided to place the patient on 4 liters per minute of oxygen. APD1=Verbal prompt by APD. APD2=0.5 second cutaneous stimulus followed by verbal prompt. APD3=1.0 second cutaneous stimulus followed by verbal prompt. APD4=1.5 second cutaneous stimulus followed by verbal prompt. Nurse1=verbal prompt by nurse. Nurse2=tactile stimulus by nurse followed by verbal prompt.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method, comprising:
    monitoring by an apparatus an individual's oxygen saturation and/or respiration, wherein the apparatus comprises a pulse oximeter and/or respiratory monitor coupled to at least one stimulus delivery device;
    delivering by the at least one stimulus delivery device a first stimulus to the individual if the individual's oxygen saturation and/or respiration falls within a first predefined range and is sustained within the first predefined range for a first predefined duration;
    delivering by the at least one stimulus delivery device a second stimulus to the individual if the individual's oxygen saturation and/or respiration falls within a second predefined range and is sustained within the second predefined range for a second predefined duration, wherein the second predefined range is indicative of more severe hypoxia or respiration than the first predefined range;
    delivering by the at least one stimulus delivery device a third stimulus to the individual if the second stimulus fails to increase the individual's oxygen saturation and/or respiration to a level above the second predefined range; and
    wherein the first stimulus comprises one or more audible stimuli, the second stimulus comprises one or more tactile stimuli, and wherein the third stimulus comprises the administration of one or more doses of a narcotic antagonist.

2. The method of claim 1, further comprising introducing by the apparatus a required lock-out period after each intervention during which no further intervention is provided.

3. The method of claim 1, further comprising notifying by the apparatus a medical professional of a status of the individual.

4. The method of claim 1, further comprising monitoring by the apparatus the individual's rate of fall of oxygen saturation, number of breaths per minute, and or heart rate.

5. The method of claim 1, further comprising recording by the apparatus a time-stamped, electronic log of physiologic data of the individual and any delivered stimulus or intervention.

6. The method of claim 1, wherein the first predefined duration is approximately 10 seconds.

7. The method of claim 1, wherein the first predefined range comprises an oxygen saturation of 85-90%.

8. The method of claim 7, wherein the second predefined range comprises an oxygen saturation of below 85%.

9. The method of claim 1, further comprising continuously monitoring the individual's oxygen saturation and/or respiration to determine if the individual's oxygen saturation and/or respiration is within the first or second predefined range.

* * * * *